United States Patent
Gebauer (10) Patent No.: US 11,867,330 B2
(45) Date of Patent: Jan. 9, 2024

(54) CONNECTOR FOR ASEPTIC CONNECTION, AND METHOD FOR CONNECTING AND DISCONNECTING SUCH CONNECTORS

(71) Applicant: Cytiva Sweden AB, Uppsala (SE)

(72) Inventor: Klaus Gebauer, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 504 days.

(21) Appl. No.: 17/056,510

(22) PCT Filed: May 29, 2019

(86) PCT No.: PCT/EP2019/064121
§ 371 (c)(1),
(2) Date: Nov. 18, 2020

(87) PCT Pub. No.: WO2019/229202
PCT Pub. Date: Dec. 5, 2019

(65) Prior Publication Data
US 2021/0215286 A1    Jul. 15, 2021

(30) Foreign Application Priority Data
May 30, 2018 (GB) ...................... 1808826

(51) Int. Cl.
*A61M 39/16* (2006.01)
*F16L 35/00* (2006.01)

(52) U.S. Cl.
CPC ........... *F16L 35/00* (2013.01); *A61M 39/165* (2013.01); *F16L 2201/10* (2013.01); *F16L 2201/44* (2013.01); *F16L 2201/60* (2013.01); *F16L 2201/80* (2013.01)

(58) Field of Classification Search
CPC ... F16L 35/00; F16L 2201/40; F16L 2201/44; F16L 2201/80; F16L 29/00; F16L 29/007; F16L 58/18; A61M 2039/1027; A61M 2039/166; A61M 2039/122;
(Continued)

(56) References Cited

U.S. PATENT DOCUMENTS 3,909,910 A   10/1975   Rowe et al.
4,019,512 A    4/1977   Tenczar
(Continued)

FOREIGN PATENT DOCUMENTS

JP   2010516342 A    5/2010
JP   2017223262 A   12/2017
(Continued)

OTHER PUBLICATIONS

Chinese Search Report for CN Application No. 201980035989.0 dated Mar. 3, 2022 (13 pages).
(Continued)

*Primary Examiner* — Aaron M Dunwoody
(74) *Attorney, Agent, or Firm* — Eversheds Sutherland (US) LLP (57) ABSTRACT

A connector for forming a substantially aseptic connection is provided, said connector having a connector member a coupling end with a coupling element for engaging a similar coupling element on a similar connector to form a seal. A method for connecting and disconnecting two such connectors is also provided.

19 Claims, 10 Drawing Sheets

(58) Field of Classification Search
CPC ........ A61M 2039/1077; A61M 39/165; A61M 39/16; A61M 39/18; A61M 39/20
See application file for complete search history.

(56) References Cited

U.S. PATENT DOCUMENTS

| | | | |
|---|---|---|---|
| 4,022,205 A * | 5/1977 | Tenczar | F16L 37/30 285/21.2 |
| 6,679,529 B2 | 1/2004 | Johnson et al. | |
| 10,314,964 B2 | 6/2019 | Heppe et al. | |
| 2010/0049170 A1 | 2/2010 | Solomon et al. | |

FOREIGN PATENT DOCUMENTS

| | | |
|---|---|---|
| WO | 2008089196 A2 | 7/2008 |
| WO | 2013004322 A1 | 1/2013 |
| WO | 2013059563 A1 | 4/2013 |
| WO | 2013147688 A1 | 10/2013 |

OTHER PUBLICATIONS

PCT International Search Report and Written Opinion for PCT/EP2019/064121 dated Sep. 9, 2019 (11 pages).
Great Britain Search Report for GB Application No. 1808826.0 dated Nov. 15, 2018 (4 pages).
First Office Action issued in corresponding Japan application No. 2020-566721, dated Jul. 18, 2023 (15 pages).

* cited by examiner

CONNECTOR FOR ASEPTIC CONNECTION, AND METHOD FOR CONNECTING AND DISCONNECTING SUCH CONNECTORS

CROSS REFERENCE TO RELATED APPLICATIONS

This application claims the priority benefit of PCT/EP2019/064121, filed on May 29, 2019, which claims the benefit of Great Britain Application No. 1808826.0, filed on May 30, 2018, the entire contents of which are incorporated by reference herein.

TECHNICAL FIELD

The present invention relates to a connector for aseptic connection and to a method for aseptic connecting, disconnecting, and reconnecting such connectors.

BACKGROUND

The biotechnology industry uses different manufacturing systems for creating aseptic and sterile connections between process containers and equipment, such as plastic bags and pumps. A known manufacturing system uses controlled environments such as clean rooms or cabinets to ensure aseptic connections during manufacture. When necessary connections are made in such a controlled environment that breaches sterile tubing and piping, the environment does not contaminate the fluid flow passages of that tubing or piping. However, maintaining a clean room is time consuming, difficult and costly to validate.

Another known manufacturing system uses disposable plastic bags connected to flexible thermoplastic tubing, which requires special connections to assure that the bags and tubes remain clean and sterile.

A sterile tube welding machine can be used to weld the thermoplastic tubing in a sterile manner without the need for a clean room, a laminar flow cabinet or similar environmental control device. After the thermoplastic tubes cool, a sterile weld is formed. A tube welding machine is however also usually limited in applicability to specific tube size and materials, such as thermoplastic tubing. Furthermore, tube welding machines are typically large, heavy, lack versatility, and expensive.

Known also are pre-sterile bags and tube sets which can be supplied with the appropriate disposable aseptic connection system fittings already in place. These connections are simple, repeatable and validatable.

Single use systems, also called disposable systems, are more and more used in the bioprocess industry. For example, separation or reaction systems such as chromatography systems, filter systems or bioreactor systems have today at least partly been provided as disposable systems. This eliminates the need for cleaning and cleaning validation before processing, in between processes and cycles or after processing before re-use as required for conventional re-usable equipment. With disposable systems cross-contamination is avoided.

Bioburden control of single-use equipment during manufacturing of the equipment itself is required to eliminate cleaning needs before bringing single-use equipment into product contact. This is usually achieved by manufacturing of single-use equipment in controlled environment (clean room), often followed by sterilisation processes (gamma irradiation). The demands of the level of bioburden control can differ for different applications. However, bioburden control to a certain degree of the equipment is not only required for some applications, but also considered as the preferable for most of the applications using disposable equipment. The production of this equipment in controlled environments is required to guarantee a low initial level of contaminants prior to the bioburden control procedure. Sterility and asepsis are terms used to define the state of a system, a piece of equipment or a fluid conduit as being in control of bioburden levels to different degrees.

Prior art describes varying apparatus for accomplishing sterile connections using disposable aseptic connectors. Typically the sterility of the connector before establishment of connection is ensured by a releasably bonded cover film which can be removed together with the cover film of a mating connector when they are connected or at a close distance to each other. Such connectors have been described in e.g. U.S. Pat. No. 6,679,529, WO 2009/002468 and WO 2013/147688, which are hereby incorporated by reference in their entireties. They are also commercially available from GE Healthcare under the name of Ready Mate™.

Although single use systems often solve the problem of providing a reliable aseptic connector, there is also a need for repeated connection such as when taking samples from a bioreactor or when reconnecting parts of a filter system or chromatography system for repeated use. This need is often met through a manifold system with several connectors that can each be connected once and that need to be welded or fused shut afterwards, or closed off by a valve or clamping off a flexible tube to prevent contamination of the system. However, this reintroduces the problems of the sterile tube welding machine mentioned above and there is still a risk for contamination of contents of the system and exposure of a human operator handling the welding machine. Further, sterile tubing welding is limited to welding of non-reinforced (non-braided) tubing, which limits the range of applicable fluid pressures. A problem with manifold systems is their physical size and in especially that fluid holdup volume increases and/or varies due to added or altered fluid path length and volume, which may be critical for certain applications such as for example chromatography, filtration and fluid sampling where low hold volume is desirable for performance, product quality or achieving a small and representative sample volume. There is therefore a need for an improved aseptic connector, particularly a connector which can be disconnected and reconnected whilst maintaining sterility of the connector and/or preserving the closed state of the connector and its aseptic barrier against the outside environment.

SUMMARY OF THE INVENTION

The object of the present invention is to eliminate or at least to minimize the problems mentioned above. This is achieved through a connector for substantially aseptic connection according to the appended independent claim, and through a method for connecting and disconnecting such connectors.

The connector according to the present invention comprises a connector member having a connection end and a coupling end, wherein the coupling end comprises a coupling element for engaging a similar coupling element on a similar connector to form a first seal, and a cover arranged to enclose the coupling end for providing an aseptic seal that separates the coupling end from a surrounding, the cover comprising at least two cover portions, each cover portion being configured to be successively positioned on or adjacent the coupling end of the connector member, wherein each cover portion comprises a seal member for engaging a similar seal member on a similar connector thereby to form a second seal when so positioned on or adjacent the coupling end of the connector member.

Thereby, a connector member can be used multiple times through the use of single-use covers that maintain the aseptic conditions for the connector and prevent contamination of a medium inside the connector, while simultaneously also protecting the environment and a human operator from exposure to said medium, which is important if infectious or toxic substances are being processed, for example. Through the invention, repeated connection of the same components is enabled while at the same time achieving the advantages of the single-use connector that provides aseptic conditions without requiring validating. There is also a considerable saving in material and space required for the connector, especially compared to a manifold connector with multiple single-use connectors.

According to an aspect of the invention, each of the cover portions comprises a protective film arranged to cover the seal member, said protective film being removably arranged. Thereby, the seal members are maintained in an aseptic condition and the protective films are removed only when the seal members of two connectors have already been coupled to each other.

According to another aspect of the invention, the coupling end comprises a stop valve for preventing a medium from flowing out through the coupling end when the connector is in a disconnected state. Thereby, the medium can be retained in the system to prevent unintentional loss so that the volume of medium can be maintained. The stop valve functionality can be achieved by various solutions, such as for example spring-loaded fluid stopping members in the flow path that close off the flow path prior or during the disconnection of the coupling end. Further, the stop valve could be engaged by the operator, for example by a push of a respective button or turning of a lever, such that the stop valve engagement is not timely and/or physically connected to the action of disconnection and separation of the connectors.

Optionally, an absorbing substance may be provided inside the portions for absorbing the medium if a small liquid leakage should nevertheless occur, which may be in form of a few droplets during disconnection, even if no fluid is applied during disconnection. Optionally, said absorbing substance may also be applied directly to the coupling end, however, external to wetted surfaces of the flow path established when a fluid connection has been made. Other means of trapping and/or isolating fluid or wetness may be provided as well as means for treating said fluid or wetness, for example for absorbents, inactivation, decontamination, and/or disinfection.

Optionally, a separate movable member on the inside or outside of the fluid connection(s) is provided that establishes the fluid tight first seal in between the connection ends after said connection ends have been brought together to form a mechanically stable connection. The use of this separate member would for example allow to reduce and de-compose forces required to establish said stable mechanical connection and establishing the seal, however, it may also enable other solutions in the connector design, such for example the implementation of gender-less connections and connector ends. Examples for said separate member are clamps, bayonet closures, complimentary tapering fittings, connectors with releasable adhesives etc.

According to yet another aspect of the invention, a holder is provided for holding at least one of the portions before use. This serves to protect the cover portions and prevent damage before use to eliminate the risk of the aseptic conditions being compromised through a tear or similar. Optionally, a second portion surrounding at least parts of the first portion is provided to provide protection of the first portion. For example, a flexible weave, mesh or cloth may be applied to provide mechanical rigidity and/or protecting the first portion from being damaged. Optionally, said second portion may be fluid tight and provide a leak protection function for additional safety and protection of the process fluid and/or the environment in case of the first portion being damaged. Optionally, leak detection features such as optical indicators or sensors may be provided. The use of wireless sensing is optional.

In one embodiment, the holder is rotatably arranged on the connector for bringing each portion in turn into a position for mounting on the coupling end. Thereby, the cover portion that is to be used can be brought into position in a convenient way and be positioned in a suitable way for connection to a similar connector.

In another embodiment, the holder is configured as a slide bar for sliding each portion into a position for mounting on the coupling end. This is also an advantageous way of positioning the cover portion before use.

According to a further aspect of the invention, each cover portion comprises a seal member coupling for forming the second seal by mating with a similar seal member coupling on a similar connector. Thereby, the seal members can be firmly attached to each other and form a secure seal that preserves the aseptic condition of the coupling. After the seal member couplings have been engaged, protective films are preferably removed from each seal member to allow them to contact each other while also forming a secure seal that avoids the drawbacks of contamination or leakage.

According to yet another aspect of the invention, the cover portions are in the form of flexible pouches. Thereby, they can easily be mounted on the coupling end of the connector and can be removed after use. Also, due to their flexibility they can be inserted into a holder or folded aside after use, as desired.

Also provided is an inventive method for connecting and disconnecting a pair of connectors having complementary coupling elements providing a sealed fluid path as defined by the appended independent claim. Through the invention, the formation of a second and a first seal enable the re-use of a connector while simultaneously providing all the advantages of a single-use connector as regards preserving aseptic conditions.

According to the method, the connectors are connected by providing a cover on each connector which surrounds at least said coupling elements of the connector pair and forming a second seal by coupling a first seal member formed on a portion of the cover of a first of the connector pair to a second seal member formed on a portion of the cover of a second of the connector pair thereby isolating aseptically the complementary coupling elements of the connectors from their environment, and forming a first seal by coupling a coupling element on a coupling end of the first connector to a coupling element on a coupling end of the second connector, wherein at least one of the coupling ends is within the coupled seal members.

In an embodiment the method may include forming a second seal by coupling a seal member on a cover portion of a first connector to a seal member on a cover portion of a second connector, and by forming a first seal by coupling a coupling element on a coupling end of the first connector to a coupling element on a coupling end of the second connector, said coupling comprising at least one of the coupling ends penetrating the seal members to enable contact with the other of the coupling ends.

According to an aspect of the invention, the coupling of the seal members to form the second seal comprises connecting the seal members to each other and removing a protective film from each of the seal members to create an essentially aseptic connection. Preferably, a cover portion comprising a seal member is mounted on the coupling end of each connector before connecting the connectors.

According to another aspect of the invention, the method comprises disconnecting the connectors by disengaging the first seal by uncoupling of the coupling elements and separating the coupling ends so that none of them penetrates the seal members. Thereby, the coupling ends can be retracted into the cover so that only the cover portions with the seal members remain connected to each other. In one embodiment of the invention, that connection can be maintained or be closed by means of a clamp or similar but the cover portions of the two connectors remain attached to each other through the second seal. New cover portions can then be mounted on the coupling end of each connector before a new connection is formed between the same two connectors or between each connector and another connector. This has the advantage of avoiding altogether the use of welding, fusing or cutting to separate the connectors from each other, and since no damage is done to the cover portions the risk for contamination or leakage is kept minimal.

According to a further aspect of the invention, the disconnecting further comprises separating the connectors from each other by separating the cover portions of the connectors through aseptic sealing of each cover portion. This can be performed through the use of a simple hand-held sealing machine and avoids the need for more complex sterile tube welding/sealing machines, while at the same time being able to separate the cover portions in a way that also securely closes the cover portions to prevent leakage or contamination. Preferably, the separation is performed through welding off, and especially by heat sealing off the cover portions, thereby achieving an operator safe disconnection between the cover portions, but other methods could also be used within the scope of the present invention. Alternatively, the cover portions could be clamped off mechanically and the separation and disconnection between the cover portions can be achieved by cutting through a clamp and clamp section or in between two clamps and clamp portions respectively. Suitable clamps could be made from plastic or metallic materials, and which are preferably ductile and deformable to a suitable degree. Optionally, said clamps may be provided or treated with means for disinfecting, decontaminating and/or inactivating any potential process fluid that may be exposed to the environment.

According to yet another aspect of the invention, the method further comprises removing the cover portion from the coupling end of each connector after disconnecting the connectors and mounting a second cover portion on the coupling end of each connector. Thereby the connector is made ready for a new connection by the mounting of a fresh cover portion so that a new second seal can be formed.

Many additional benefits and advantages of the invention will become readily apparent to the person skilled in the art in view of the detailed description below.

DRAWINGS

The invention will now be described in more detail with reference to the appended drawings, wherein FIG. 1 discloses a first and second connector according to a preferred embodiment of the present invention in a planar view.

DETAILED DESCRIPTION

Figure 1:
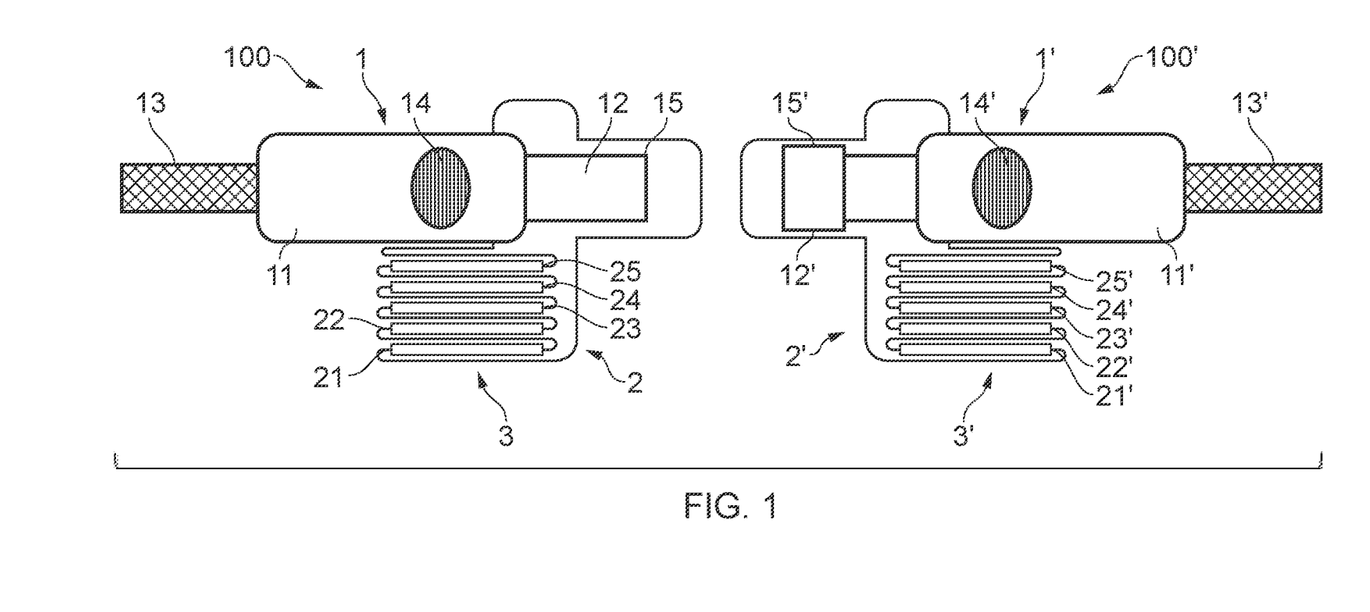

FIG. 1 discloses two connectors according to a preferred embodiment of the present invention, a first connector 100 and a second connector 100'. In the following, it is to be noted that what is said with reference to one connector is also generally applicable to the other.

Thus, a first connector 100 comprises a connector member 1 having a connection end 13 and a coupling end 12. The connection end 13 is generally connected to a tube or pipe through which a medium can flow. The connection 13 as well as said tube or pipe are suitably designed to accommodate for a desired operating pressure and/or a range of operating pressures. If connection 13 comprises flexible tubing the tubing may be reinforced, for example by braiding, to enable higher operating pressure compared to non-reinforced flexible tubing.

The connection end 13 and the coupling end 12 are both connected to a connector member body 11 in such a way that the medium can flow from the tube or pipe and through the connection end 13, connector member body 11 and out from the connector through the coupling end 12. The connector member 1 also comprises a coupling element 15, here shown as a release button 14 for releasing a spring-loaded coupling that has been established between the coupling end 12 of one connector to a coupling end 12' of a second connector 100'. The coupling element 15 may however be in another form, such as a screw coupling with a thread or another kind of fastening mechanism, as long as it is able to establish and release a connection. Suitable couplings also include bayonet coupling having short angle rotation or snap-on clamps, and the coupling element 15 may be located at a position shown in FIG. 1 or alternatively be located closer to the coupling end 12. Other known coupling mechanisms could be employed with equal utility.

The first connector 100 also comprises a flexible folded cover 2 that encloses the coupling end 12 and provides a barrier that prevents leakage from the coupling end 12 as well as preventing contamination of the components inside the cover 2 from the environment outside the cover 2. The cover 2 comprises a number of cover portions, each successively positional in an operative position and each cover portion includes a seal member 21, 22, 23, 24, 25 that can be mounted in turn on or around the coupling end 12 as will be described in detail below. Each seal member is a formed from a resiliently deformable annulus overlaid with a peel-off protective film such that its inner open area can be exposed by removal of said film. The film is folded such that it can be removed by pulling, even when two seal members are held together side by side. Alternatively, the seal members may be in the form of septa, but they will still have the overlaid protective films. It is important that the protective films are held to the seal members so that they cover all areas of the seal that would otherwise have been exposed to the potentially contaminated surrounding environment.

The cover portions with seal members 21, 22, 23, 24, 25 are, in this embodiment, held by a holder 3, in a concertinaed manner for successive deployment. The cover material which connects the successive seal members 21, 22, 23, 24, 25 is substantially impermeable, and where this material interconnects the seals, is of sufficient dimensions to allow said deployment without pulling the next seal in the sequence out of the storage position shown. The interconnecting material can be stretchable, bunched-up, for example pleated, to allow manual manipulation of successive seals.

The second connector 100' comprises the same components as the first connector 100, and in this drawing the coupling end 12', connection end 13' and coupling element 15' along with the connector member 1' are shown. The method for connecting and disconnecting the two connectors 100, 100' will now be described in more detail with reference to FIGS. 2-6.

Figure 2:
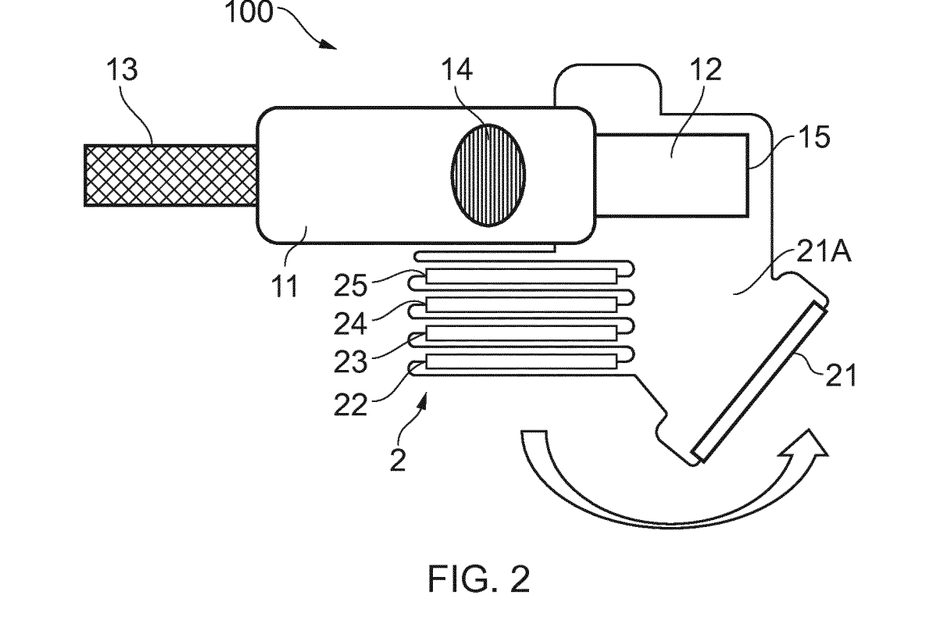
FIG. 2 discloses a connector of FIG. 1 during mounting of a cover portion on a coupling end.
Figure 3:
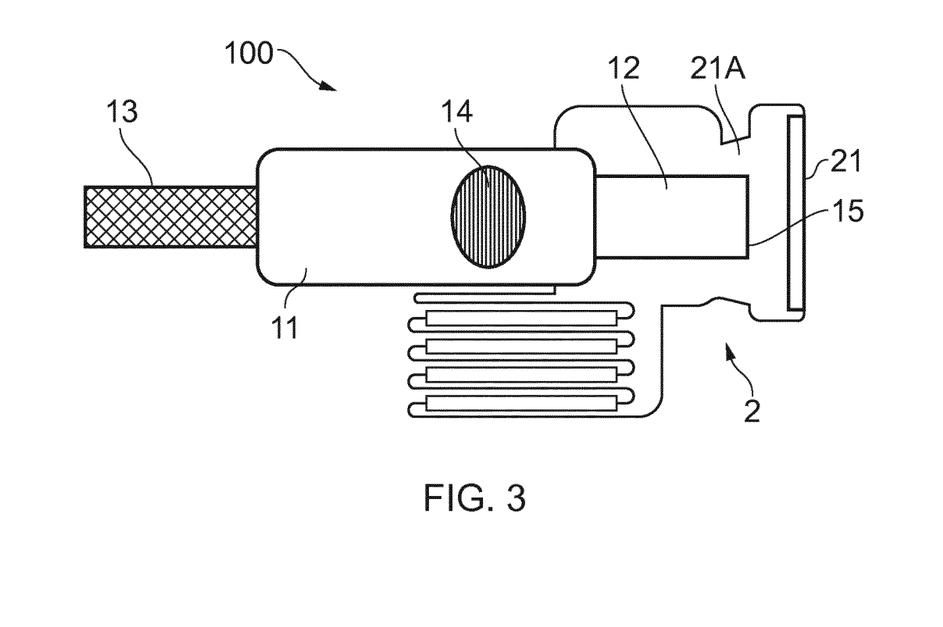
FIG. 3 discloses the connector with the cover portion mounted on the coupling end.

FIG. 2 shows mounting of a first cover portion 21A, having a seal member 21, on the coupling end 12 of the connector 100. In this embodiment, the first cover portion 21A is moved in the direction of the arrow from a side position on the connector 100 to be positioned adjacent the coupling end 12. The first cover portion 21A is in this embodiment a flexible pouch made from a thin but durable plastic material and it can be moved by hand to be mounted on the coupling end 12 or can alternatively be moved by manipulating a holder 3 that can be arranged in a rotatable or slidable way so that the first cover portion 21A is rotated or slid into place at the coupling end 12. In FIG. 3, the first cover portion 21A is positioned at the coupling end 12 with the seal member 21 covering the end of the coupling end 12.

Figure 4:
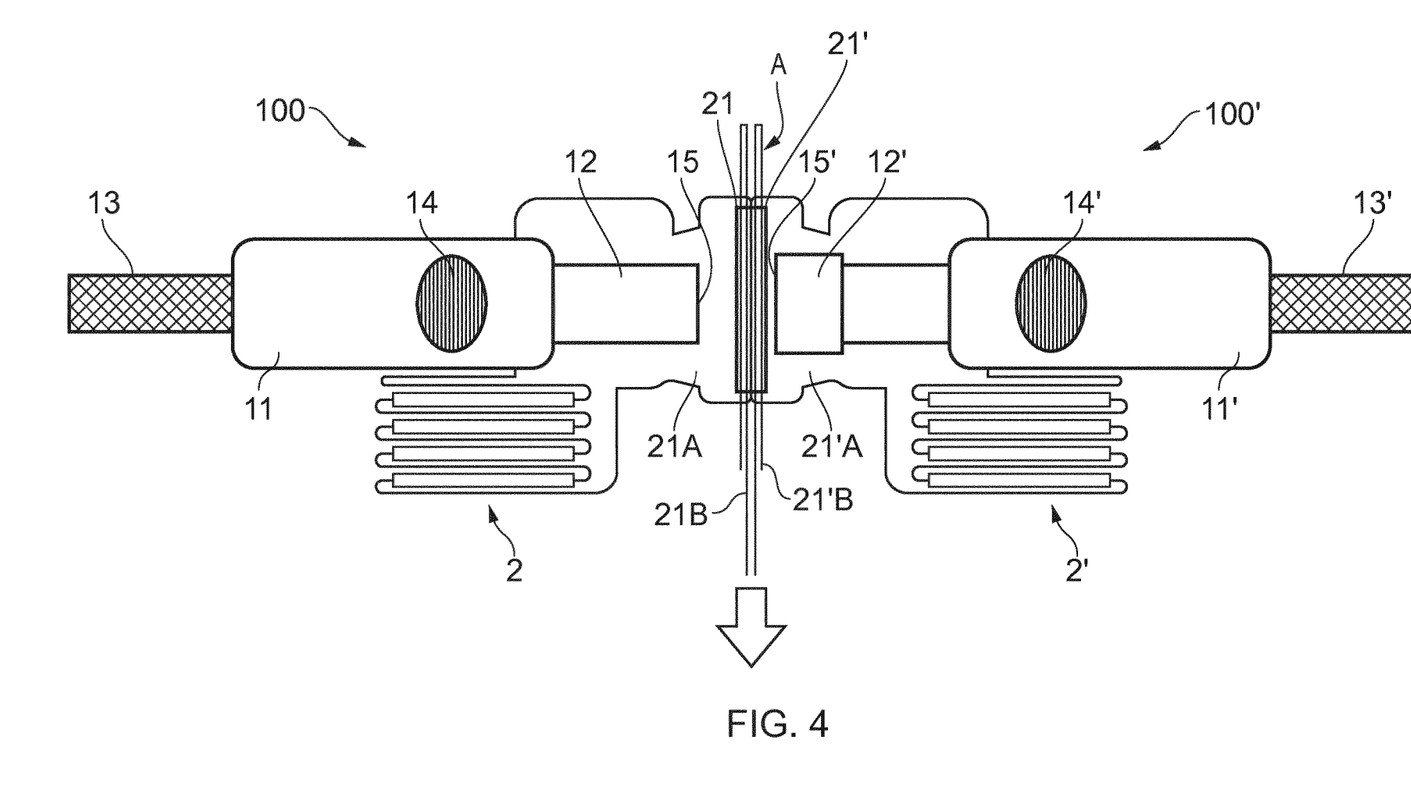
FIG. 4 discloses the first and second connector during forming of a second seal.

In FIG. 4, the first and second connectors 100, 100' are positioned to face each other with seal members 21, 21' facing each other. A second seal A is formed by attaching the seal members 21, 21' to each other, preferably by use of seal member couplings (not shown) that may be in the form of a snap coupling, adhesive coupling, or any other suitable coupling that enables the seal members to be secured to each other around their periphery. The seal members are preferably circular in shape but could also be another shape such as oval or rectangular. As the second seal A is formed, the protective films 21B, 21'B that have been covering each of the seal members 21, 21' are removed by pulling in the direction of the arrow to free the seal members 21, 21'. The second seal A thus comprises a coupling of the seal members 21, 21' to each other in such a way that their peripheries abut each other and form an aseptic connection that prevents leakage from inside the cover portions 21A, 21'A and also prevents contamination to any medium present inside the cover portions 21A, 21'A. In some embodiments, the seal member couplings may be in the form of a separate clamp or holder, or in the form of heating to make a material applied at least to the periphery of the seal members to melt and form a secure connection after cooling.

Figure 5:
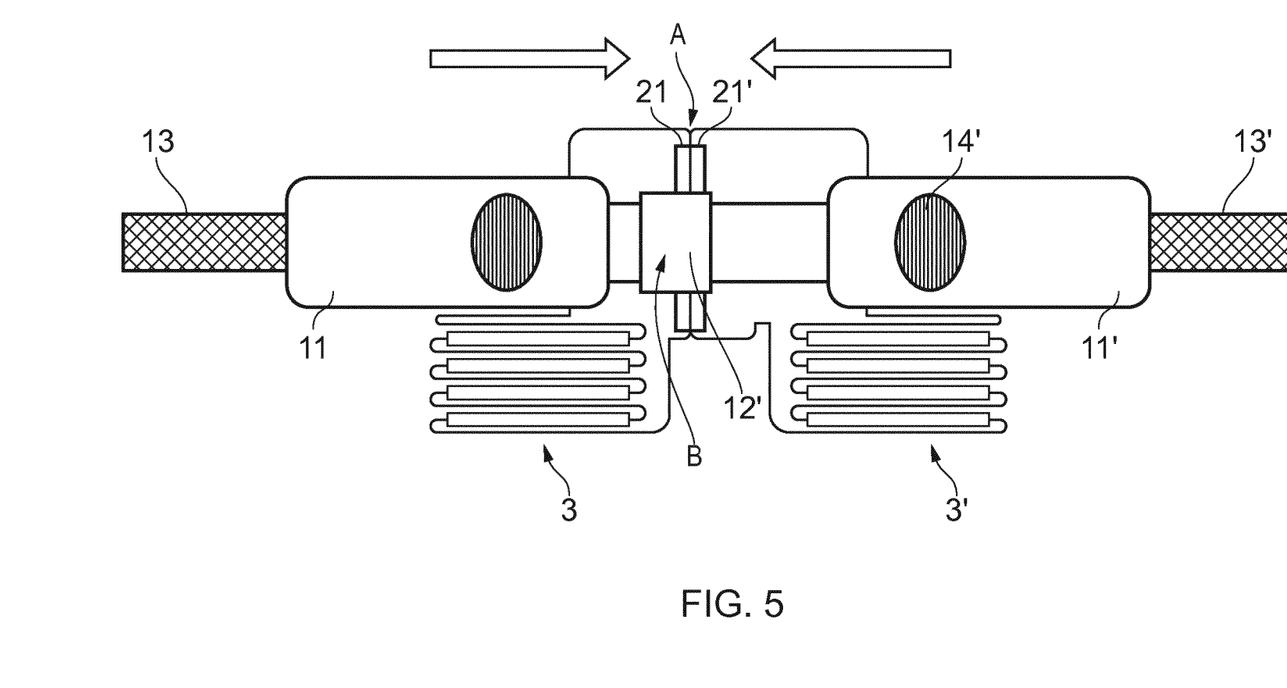
FIG. 5 discloses the first and second connector during forming of a first seal.

FIG. 5 discloses formation of a first seal B by moving the connectors 100, 100' towards each other in the direction of the arrows so that the coupling ends 12, 12' meet and couple. In order to achieve this, where the seal members are formed as a septum of continuous material, at least one of the coupling ends 12, 12' penetrates the seal members 21, 21' and where the seal members are in the form of an annulus, the coupling ends simple occupy the inner opening of the annulus. In this embodiment, the coupling ends 12, 12' are disclosed as male and female but they could also be non-gendered. In a non-gendered version, two substantially identical coupling ends 12, 12', would be connected, for example by a bayonet principle with short rotation angle, and a fluid tight first seal B may be achieved in a subsequent step, for example by movement of inner or other member(s) of the connection, which may be done prior or in the same step as opening the optional stop valves.

As the first seal B is formed, the coupling ends 12, 12' engage each other and the coupling elements 14, 14' couple them in a releasable way.

After the second seal A and the first seal B have been formed, a medium such as a gas or a fluid can flow from the first connector 100 to the second connector 100' or vice versa, and the cover portions 21A, 21'A provide a protective cover around the coupling ends 12, 12' of the connectors.

Different embodiments are feasible for providing first seal B, such as axially acting, or radially acting seals or angled seals, such as tapered fitting arrangements and combinations of these. In certain embodiments, especially when providing connectors for higher fluid pressures, radial sealing arrangements may be preferable as axial sealing arrangements require an active clamping force to maintain the seal and fluid tightness. A radial O-ring seal, for example, may provide a fluid tight seal after coupling ends 12 and 12' have been engaged such that there is only an axial fixation or locking of the connectors and their connector ends by the coupling elements 14, 14' required. Details of the coupling mechanisms are not shown here, however, numerous solutions including spring loaded latch functions, bayonet locking features, locking taper fittings etc. are feasible.

Figure 6:
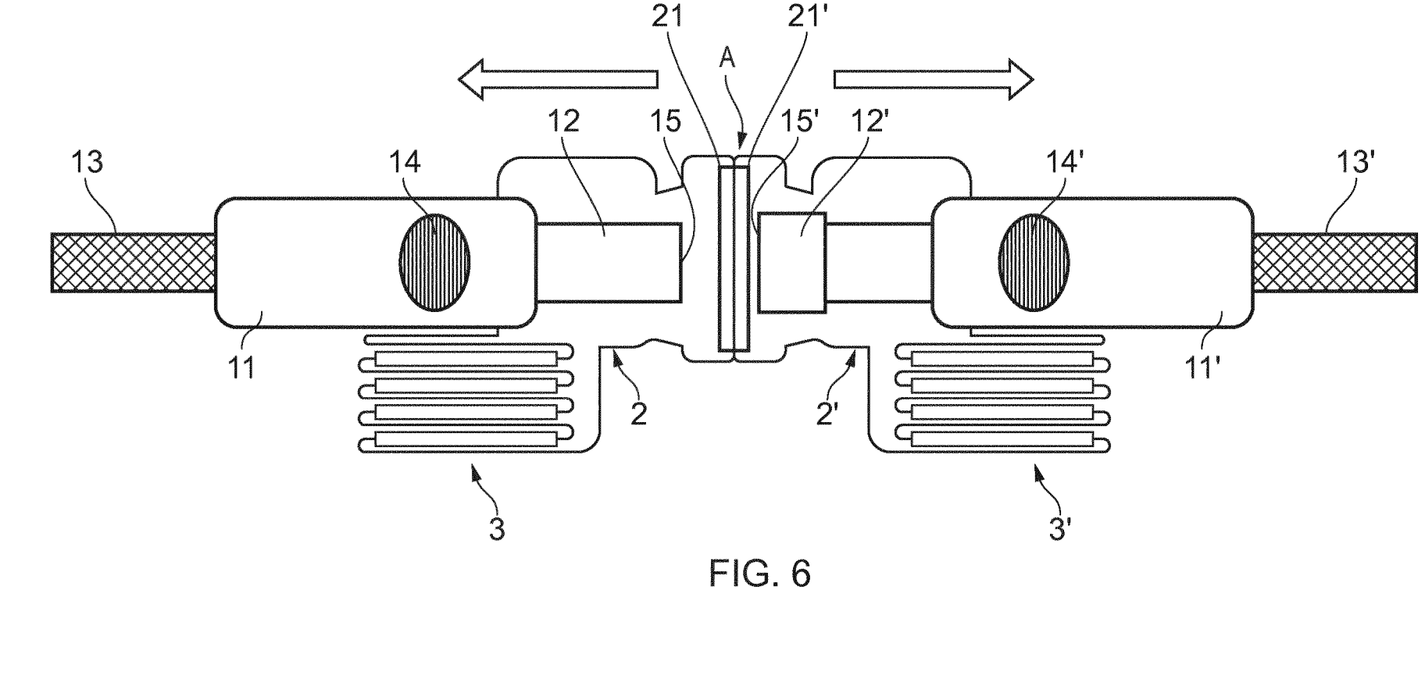
FIG. 6 discloses the first and second connector during disconnection of the first seal.

The disconnection of the connectors 100, 100' is performed through the decoupling of the coupling ends 12, 12' as shown in FIG. 6. There, the first seal B has been broken a decoupling the coupling ends 12, 12' and pulling the connectors apart. The decoupling is performed by using the coupling elements 14 in order to release the coupling ends 12, 12' from each other. When the connectors are pulled in the directions of the arrows of FIG. 6, they are retracted through the seal members 21, 21' so that each coupling end is inside their respective cover 2, 2'. In one embodiment, the cover 2, 2' holds an absorbing substance that absorbs any liquid medium that has leaked from the coupling ends 12, 12' after they were decoupled. Preferably, each connector 100, 100' also comprises a stop valve that prevents such leakage and said stop valve can be activated through the coupling elements 14, 14' or separately, as is suitable for a particular application.

In one embodiment, the second seal A remains in place after the first seal B is disengaged and the coupling ends 12, 12' retracted. A clamp or other stop can be applied to the cover portions 21A, 21'A in order to prevent any medium flowing from one connector to the other 100, 100', but the connection through the second seal A can remain and the cover portions 21A, 21'A folded to a side of the coupling ends 12, 12' before a fresh cover portion with a fresh seal member 22, 22' is mounted on the cover ends 12, 12'. The connectors 100, 100' can then be connected again, either to each other or to other connectors.

However, in the preferred embodiment the cover portions 21A, 21'A are disconnected from each other. There, the connectors 100, 100' have been separated further so that the cover portions 21A, 21'A and their seal members 21, 21' are exposed for easy access. A separation is then performed and each cover portion 21A, 21'A aseptically sealed, preferably through a heat sealing that may or may not be combined with a separate cutting action. Thereby, separation may be performed at lines 4, 4' by applying a hand-held heat sealing device that heats the cover portions 21A, 21'A to melt and seal the material while simultaneously cutting at the lines 4, 4'. Thereby, an aseptic closure of the cover portions 21A, 21'A is achieved so that the inside of the cover 2, 2' is maintained separate from the surroundings of the connectors 100, 100' and the lines 4, 4' form a third seal C. Heat sealing the cover portions 21A, 21'A is easy since a thin, flexible plastic material can be used for the cover 2 compared to a heavier and sturdier material that is required where medium should be able to flow at an elevated pressure, such as through the coupling ends 12, 12'. To cut the cover portions 21A, 21'A is then significantly easier than it would be to cut the coupling ends 12, 12' and this is also a significant benefit of the present invention.

After the separation of the cover portions 21A, 21'A, they can each be moved to a side of the coupling ends 12, 12' and a second cover portion 22A, 22'A can be mounted on the coupling ends 12, 12', either by manually moving them to the coupling ends and aligning the seal members 22, 22' with the coupling ends 12, 12' or by using a holder 3, 3' to position them as described above.

In some applications, only one of the connectors 100, 100' may be intended for establishing a new aseptic connection subsequent to disconnecting from a previous connection. Therefore, it may be sufficient to form only one single third seal C in a disconnection process close to the connector 100 intended for re-use and to leave the seal members 21, 21' forming the first seal B still attached to the other connector 100'. In some applications it may not even be necessary to aseptically seal the connector 100' not intended for re-use, although that would be for applications where the risks to the operator of exposure to a medium inside the connector are low.

In some applications it is desirable to avoid a medium standing still inside the connectors 100, 100' after the connectors 100, 100' have been disengaged from each other. In such applications, such as for instance when taking samples from a bioreactor a return flow can be arranged on the inside of the connector member body 11 so that a constant flow to and from the connector 100 is maintained at times when the connector 100 is not connected to another.

Two examples of applications of the present invention will now be described briefly.

In a first application, the connector 100 of the invention is used in a bioreactor system where repeated sampling is required and where it is desirable to maintain a constant volume of the bioreactor. It is advantageous to use the return flow inside the connector 100 as mentioned above, to avoid a dead-leg forming where cells from the bioreactor can be held motionless and with limited access to nutrients, causing cell death.

In this application, the connector may be mounted with the connection end 13 fastened directly in a wall of a cell bag or alternatively at an end of a pipe or hose leading from the bag. When a sample is to be taken, the connector 100 is connected to a similar connector 100' by forming the second seal A and the first seal B as described herein, and a predetermined volume of fluid is removed from the bioreactor. Afterwards, the first seal B is disengaged and the cover portions 21A, 21'A are separated by heat sealing at the lines 4, 4' to aseptically seal the covers 2, 2'.

When another sample is to be taken from the cell bag, the connector 100 is once again connected but now with the second cover portion 22A serving to form the second seal A. In this manner, the connector 100 can be used a plurality of times while still maintaining the aseptic conditions and preventing leakage from the connector as well as contamination of the contents of the cell bag. This represents a significant advantage compared to the prior art solutions and provides a cost effective as well as time effective solution.

In a second application, the connector 100 of the invention is used in a filter system where solutions are inserted at different time from supply containers. When in use, a connector 100 of the system is connected to a similar connector 100' of a supply container and allows a fluid to be received by the filter system. Afterwards, the connectors 100, 100' can be disengaged in the manner described above and the connector 100 can be connected again to another supply container holding another solution. This eliminates the need for conventional manifold connectors that have previously been used in this area, as well as in the field of bioreactors briefly described above.

In another embodiment of the invention, a plurality of connectors according to the invention can be mounted together with their connection ends 13 leading to the same hose or conduit. This represents a manifold connector where each of the connectors 100 can be used a plurality of times with separate cover portions and enables the creation of a manifold connector that can be used repeatedly many times. The total number can be decided through the selection of the number of cover portions 21, 22, 23, 24, 25 of the cover 2 and can be altered as suitable.

In another embodiment of the invention, a plurality of connectors can be connected in series to increase the number of aseptic connections that can be made. For this purpose, a short length connector piece with two aseptic connections at each side may be employed to extend the number of aseptic connections. Said connector piece, or extender, may be designed with a only a single seal member at one end intended to connect to the fluid line to be extended, and multiple aseptic seal members at the other end, which is intended to provide new (fresh) multiple aseptic connectivity.

Figure 7:
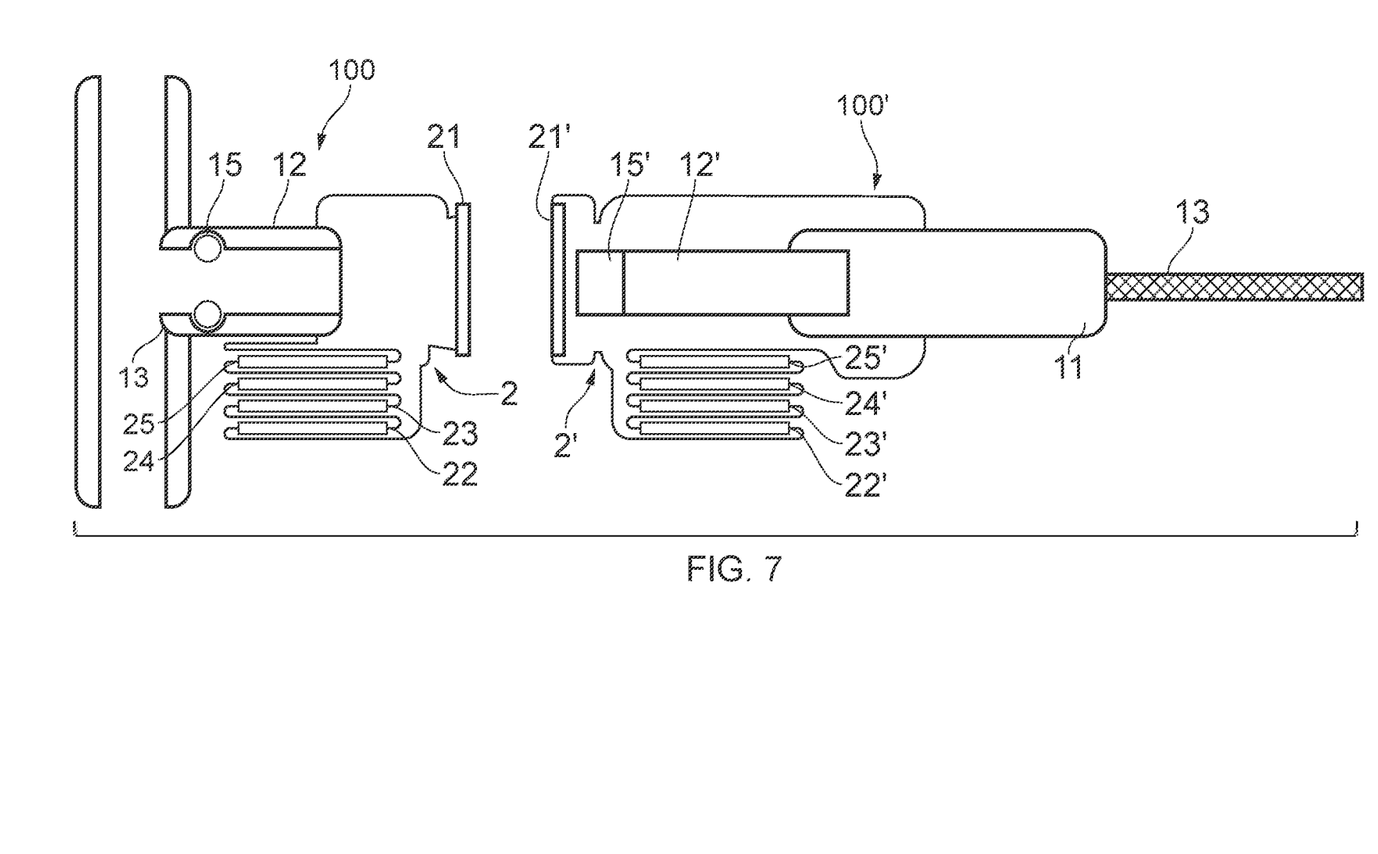
FIG. 7 discloses an alternative embodiment of the invention, where a connector is connected to a sensor port in a fluid line.
Figure 8:
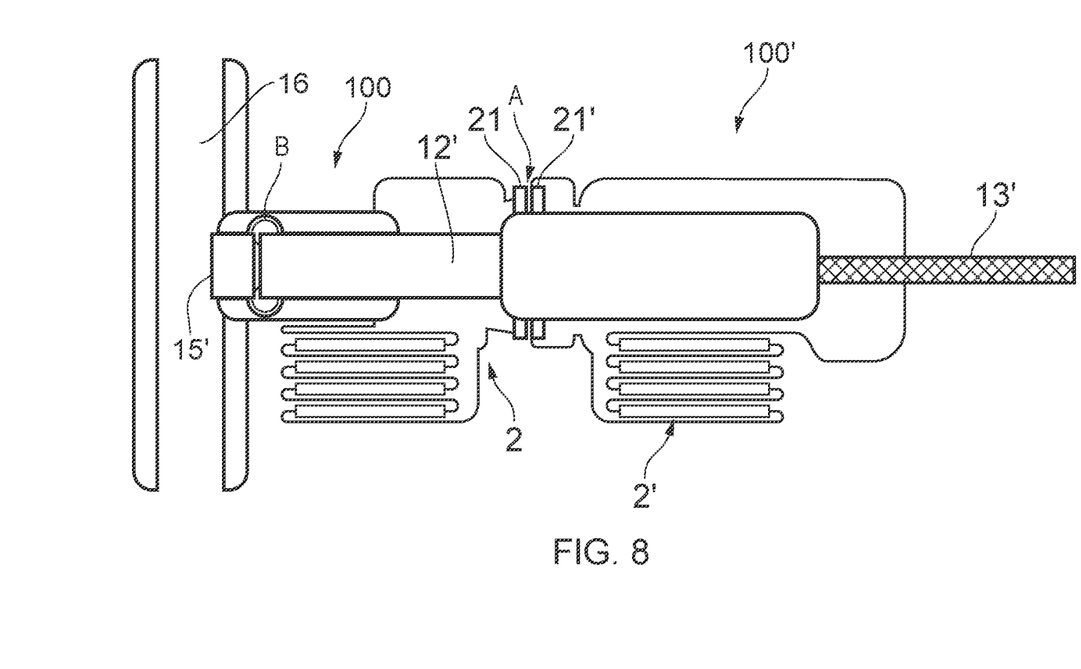
FIG. 8 discloses the alternative embodiment of FIG. 8, where the connector is coupled to a second connector to form the first and second seals of the invention.

FIGS. 7-8 show an alternative embodiment of the invention, where the first connector 100 is at an end of a fluid line 16 and the second connector 100' comprises a probe on the coupling end 12' that is to be inserted into the fluid line 16. The main difference between this embodiment and the preferred embodiment described above is that the coupling end 12 of the first connector 100 comprises a coupling element 15 in the form of a sealing such as an O-ring that forms the first seal B through interaction with the coupling element 15' of the second connector 100'. Otherwise, the connectors 100, 100' are similar to those described above.

The pair of connectors 100, 100' of the alternative embodiment are coupled by the second seal A being formed by the seal members 21, 21' and the coupling end 12' of the second connector 100' being inserted into the coupling end 12 of the first connector 100 so that the coupling element 15' of the second connector 100' can interact with the coupling element 15 of the first connector to form the first seal B.

Figure 9:
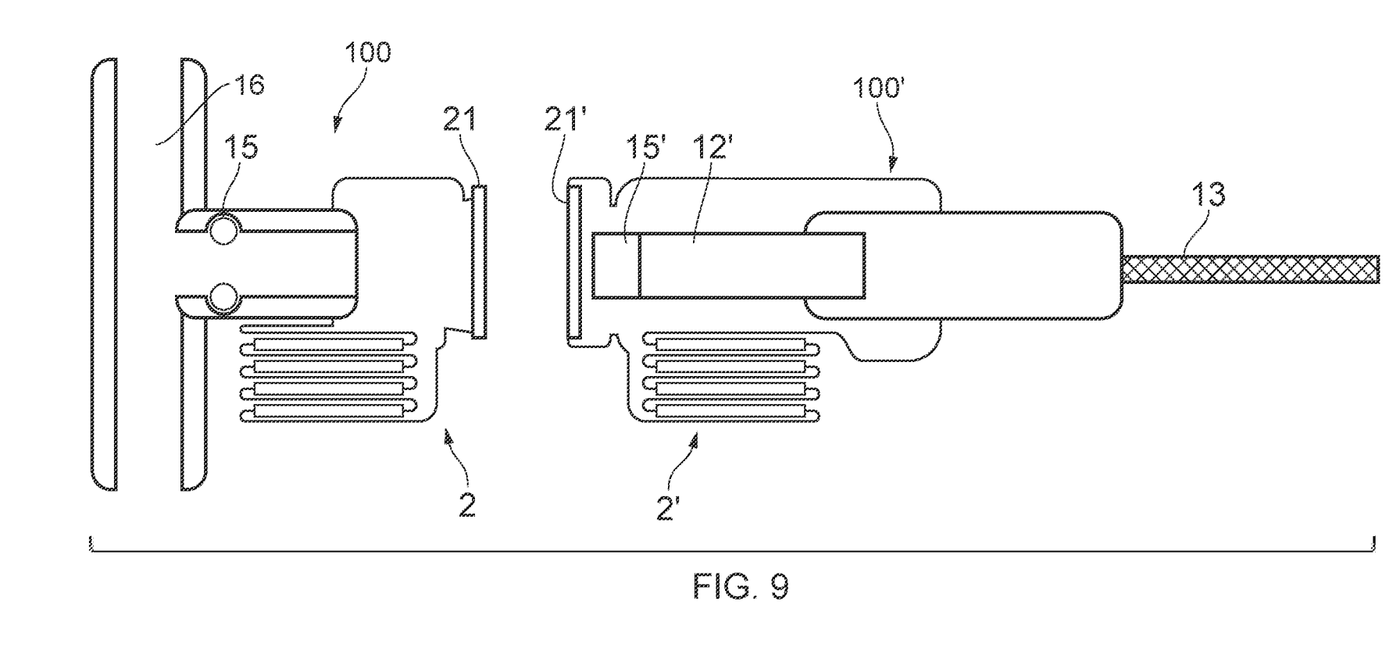
FIG. 9 discloses an embodiment where the second connector is a single-use connector.

In a modified version of the alternative embodiment, the first connector 100 could alternatively be formed on a vessel port of a bioreactor and the second connector 100' could be a sensor with a probe portion at the coupling end 12 that is inserted into the bioreactor in the same way that the probe of the alternative embodiment of FIGS. 8 and 9 is inserted into the fluid line 16.

The disconnection of the alternative embodiment is performed in the same way as for the preferred embodiment and all the alternatives described for that embodiment are equally applicable to the alternative embodiment.

In some embodiments, the second connector 100' can be a single-use connector having a cover 2' as described above but said cover 2' only comprising one cover portion 21A' with a seal member 21'. This situation is shown in FIG. 9. The first connector 100 could thus be used to aseptically connect one connector used multiple times with a series of single-use disposable conduits, for example in place of a multiport valve in disposable equipment, or to connect a reusable connector again and again to consumable items such as a filter or chromatography column. In such cases, only a final heat seal of the cover is needed on the reusable connector side.

Figure 10:
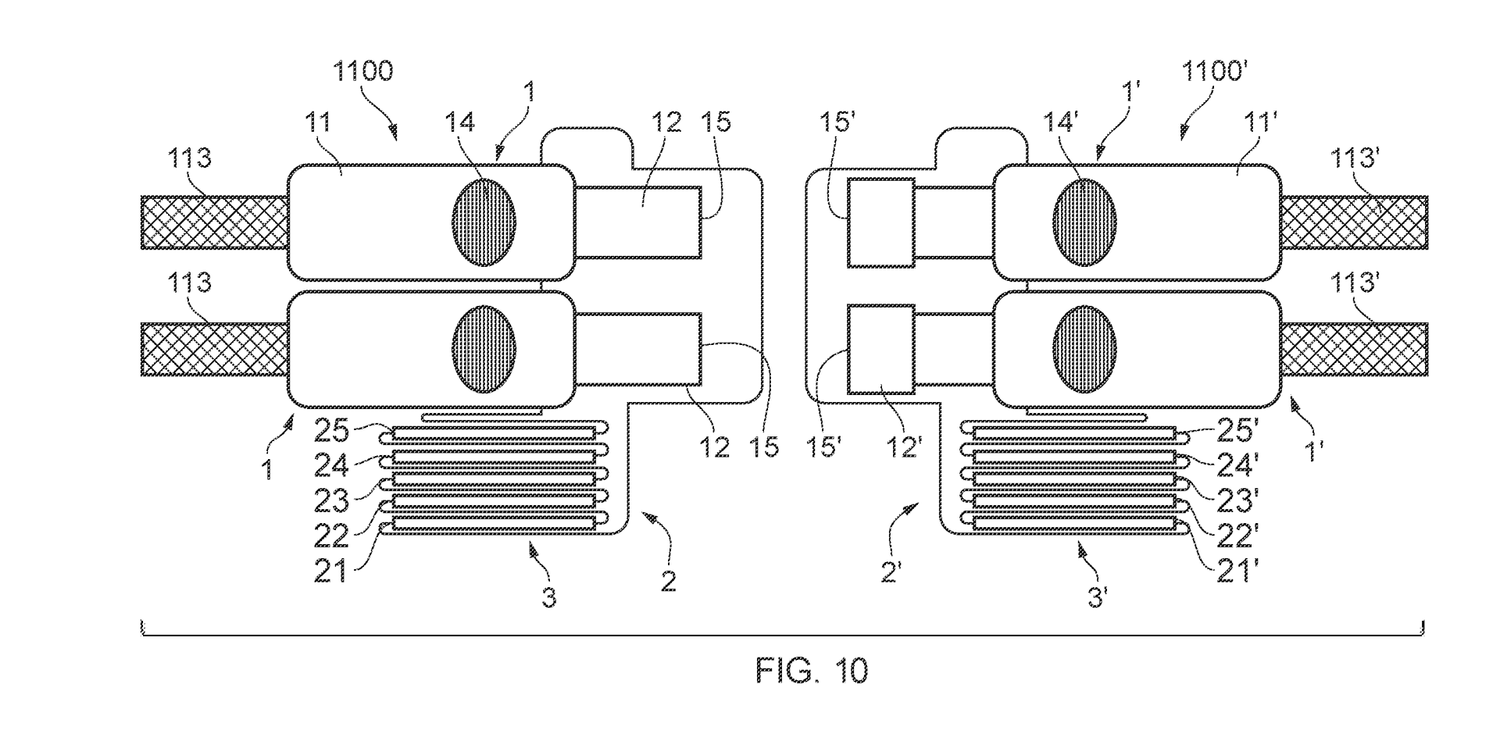
FIG. 10 shows a multi-connector embodiment.

FIG. 10 shows another embodiment of the invention. In this drawing, the connector pairs 1100 and 1100' comprise two connectors, for example feed and return tubing 113,113'. The seal members 21-25 and 21'-25' are similar in construction to the seal members described above but are made larger to accommodate the increased number of connectors—two pairs in this case, but other amounts could be used, form example three or more connectors. The operation of the seal members is the same as described above. Whilst the two pairs of connectors are shown as separate pieces sealed together, it would be equally useful to combine paths to be sealed into a single manifold block, for example where fluid and/or or electric connectors are combined into one connector block.

Figure 11:
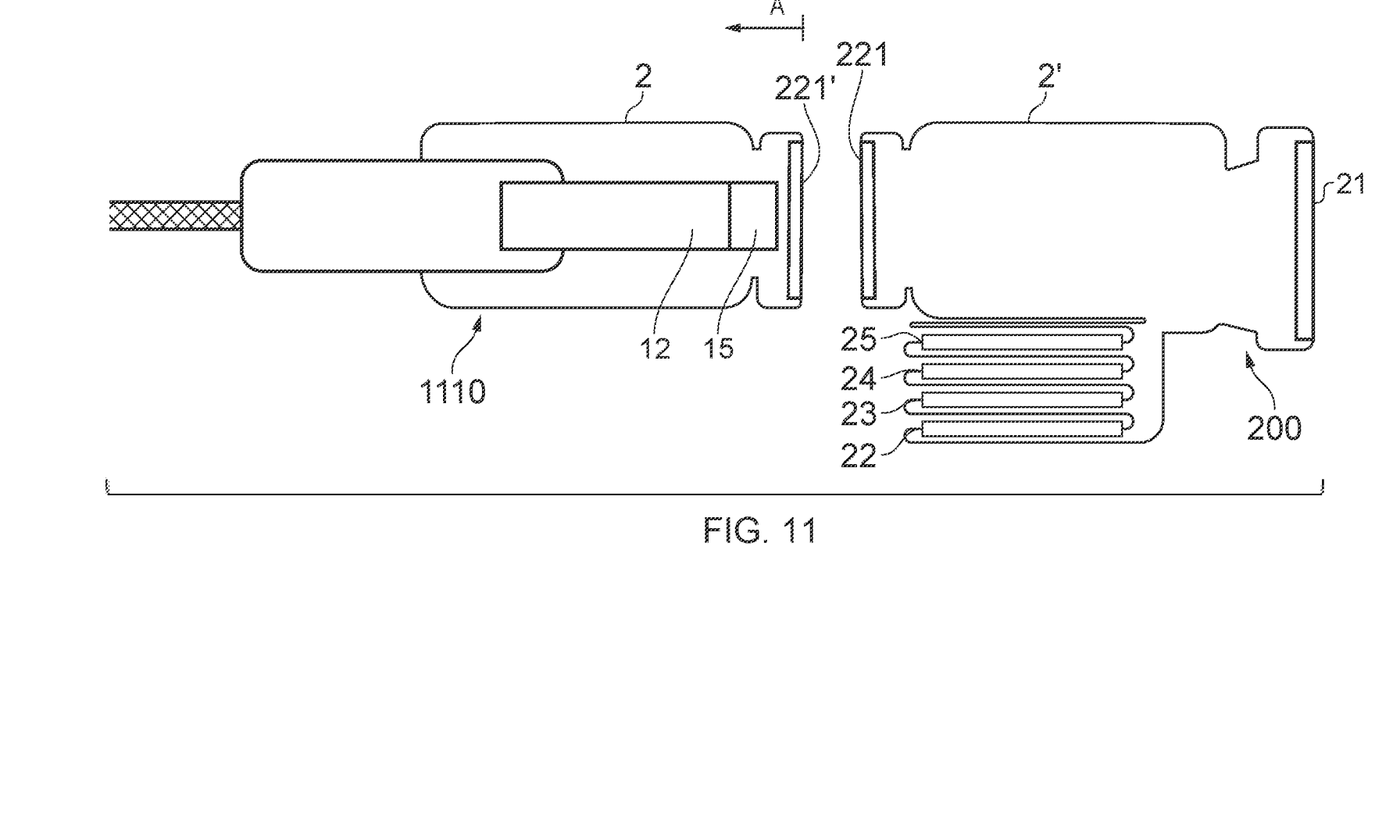
FIG. 11 shows another embodiment of the invention.

FIG. 11 shows another embodiment where the seal members 21-25 are mounted to a discrete cover portion 2, which forms an adapter 200. Those seal members are intended to function with complimentary seals as described above. The adapter 200 includes an additional sealing region 221 which is intended to connect to another similar seal 221' on a connector 1110 such as a single use seal. In this case the seals 221 and 221' need not be the peel-back type described above. The function of the seals 221 and 221' is to provide a lower cost connection, which can be made in order to selectively adapt an otherwise single use connector 1110 into a multiple use aseptic connector. Once made the seal between seals 221 and 221' can be moved in the direction of arrow A over the connector 1110 so that the seals 21-25 can be positioned around the coupling element 15 of connector 1110, so that the connector length does not need to be especially extended. The cover portion 2' of the connector 1110 and cover portion 2 of adapter 200 act as described above to isolate those parts from their surrounding environment in the manner described above. It will be apparent to the skilled person that the adapter 200 can be made with any seal 221, if it can be sterilized after fitting for example a mechanical seal such as a push-on or threaded fitting could be used, but to maintain sterility, a peel back seal of the type mentioned above is preferred. Also, whilst the adapter is intended to isolate a fluid connector 1110 or the like, the adapter 200 could be employed with a broader range of couplings. It will be apparent also to the skilled addressee that the seal 221,221' could also be a multi-use type seal of the type described above in relation to seals 21-25 and 21' to 25'.

In some embodiments, a sterile vent filter is integrated into the connector to allow a volume adjustment of the cover 2 during different steps of the operation, such as for example the displacement of cover portions, the displacement of the connector parts during connecting and disconnecting and during sealing off after disconnection. However, in practice the internal volume will not change significantly, so a vent is not essential.

In another embodiment, the internal volume of the cover 2 may be subjected to gas flow for creating a positive pressure slightly higher than the ambient pressure outside cover 2. This moderate overpressure may facilitate the operation of the connector parts and extension of cover for certain operating step, and a slight overpressure provides also additional aseptic security to avoid contamination of the internals of cover 2, connector and process fluids. Said gas flow for pressurizing cover 2 is suitably sterile filtered and excess gas flow may exit cover 2 through a second sterile vent filter. The second vent filter for the exhaust gas may be selected to provide suitable hydraulic resistance to control the pressure difference to ambient pressure, alternatively a check valve of defined release pressure may be applied in the exhaust gas fluid path.

In some embodiments, and indicator or sensor may be provided in cover 2 for sensing conditions in the cover, either prior during or after a connection or disconnection has been made. For example, said indicators or sensors may provide leak detection functionality or pressure assessment. In another embodiment, a sensor may be provided to indicate the state of the connector, such as for example different physical positions and/or states of the connectivity, the positions and/state of optional valves (open/close) or coupling elements 14, 14. The use of wireless sensing is optional and in some embodiments preferable, and wireless sensors may utilize various energy harvesting techniques to provide autonomy and cost efficiency for the sensing elements. In some embodiments, sensing elements at the connector may be combined with externally applied senor or transmitter components, which may reduce cost and complexity of the connector itself.

In some embodiments, the connector or parts of it such as for example cover 2 may be transparent, or include a transparent window, to facilitate visual inspection, operation etc.

In some embodiments, flexible parts, for example cover 2 may be provided with a lining at the inside and/or outside to decrease friction in between folded sections of the cover and/or to avoid stickiness or adhesion in between folded surfaces. Instead of a lining made form same or different material than the flexible cover 2, a surface treatment may be applied, or the material of the flexible part may be designed with a specific surface profile providing a desired roughness, pattern, corrugation etc.

In some embodiments, the connector may be provided and/or utilized as a single connect and/or disconnect aseptic connector.

The present invention discloses connectors for aseptic connection and a method for connecting and disconnecting two such connectors. The connectors are suitable for use as fluid connectors, for example for processing liquids and gases, but could also be used for non-process fluid connections such as a pneumatic connection for a gas flow or non-fluid connections such as an electrical connection for transferring electrical current. The suitable areas of use are any areas where aseptic connection is desired, and apart from the applications described above it would also be suitable to use the present invention for other fields, e.g. for electrical connections in environments where cleaning, sterilizing and disinfecting are difficult, such as in clinical/surgery applications for instance. Thus, instead of protecting the internal of the connector from the outside and environment, as typically desired for protecting and shielding a process fluid, the cover may also be used to protect the outside environment from whatever shall be connected at the connectors inside.

Further, whilst just one aseptic fluid connector has been described above and illustrated, it is entirely possible a pair, or more, of adjacent connectors could be used, where the aseptic cover is used to encompass that pair or more of connectors. Such connectors could be discrete components, but it is preferred that they would be formed in a connected molding, for example a unitary molding, such that complementary fluid connection elements can be brought together easily by virtue of their spacing being maintained by the molding, to form plural generally aseptic fluid paths, which can be aseptically formed.

Turning to the use of the aseptic connections, couplings and/or the cover portions, at least one or several items among connections, couplings, cover portions or seal members may be marked for easy identification and traceability during production, distribution, and/or inspection in a laboratory, production or manufacturing environment, for example. Suitable markers and identifiers can be numbers or content on article and serial number, connection ID, connection status or similar, and said markers and identifiers can be provided in form of mold imprints, printed labels or bar codes, color codes, or as optically or electronically readable markers, such as RFID tags, which further may be compatible with mixed reality tools for workflow instructions, execution and data monitoring and recording. Said markers or tags may be writable to allow to record the history of use for parts. Markers or tags may be applied to connectors and/or subcomponents of the connectors, for example they may be applied to individual cover portions. Further, connections, couplings, cover portions or seal members may be provided with active or passive sensing and/or transmission devices, which may be wired or wireless, and which may provide information on properties or status of said components and/or fluid properties and/or properties.

It is to be understood that the invention is suitable for use in many technical fields where an aseptic connection between two compartments via a multiple use seal member is desirable or where connectors, lines or other communication through and/or within an aseptic seal member is desirable. These technical fields include many areas in medicine, chemistry and technology where samples are taken, or substances are transferred from one container to another via a seal member or similar. The invention may also be used for connecting and/or disconnecting compartments to enable the aseptic transfer of any material or matter in between said compartments, such for example the transfer of objects in between clean rooms or controlled environments. The description of some of these applications herein are merely to be seen as examples, as will be readily understood by the skilled person.

It is also to be noted that features from the various embodiments described herein may freely be combined, unless it is explicitly stated that such a combination would be unsuitable.

In another embodiment, a standard connector may have 2 aseptic connections and seal members, where the second position offers a 'backup' option to allow for reconnection in case of operator failure or if a failure in a system requires a single re-connection, for example. This second aseptic connectivity can the also be utilized with our 'connectivity extender' to upgrade for multi-connectivity.

The invention claimed is:

1. A fluid connector for substantially aseptic connection, said connector comprising:
   a connector member having a connection end and a coupling end, wherein the coupling end comprises a coupling element for engaging a complementary coupling element of a complementary connector to form a first seal, and
   a cover arranged to enclose the coupling end for providing an aseptic seal that separates the coupling end from a surrounding, the cover comprising at least two cover portions, wherein each cover portion comprises a respective seal member configured to aseptically engage with another seal member of the secondary connector to form a seal, and wherein each cover portion is configured to be successively positioned such that a new second seal can be formed when a fresh cover portion is deployed on or adjacent the coupling end of the connector member.

2. The connector according to claim 1, wherein each of the cover portions comprises a protective film arranged to cover the seal member, said protective film being arranged to be removable from a corresponding seal member when two seal members are brought together for said engagement.

3. The connector according to claim 1, wherein the coupling end comprises a stop valve for preventing a medium from flowing out through the coupling end when the connector is in a disconnected state.

4. The connector according to claim 1, further comprising an absorbing substance inside the cover portions for absorbing a liquid medium.

5. The connector according to claim 1, further comprising a holder or holding at least one of the cover portions before use.

6. The connector according to claim 5, wherein the holder is rotatably arranged on the connector for bringing each cover portion in turn into a position for mounting on the coupling end.

7. The connector according to claim 5, wherein the holder is configured as a slide bar for sliding each cover portion into a position for mounting on the coupling end.

8. The connector according to claim 1, wherein each cover portion comprises a seal member coupling for forming the second seal by mating with a similar seal member coupling on a similar connector.

9. The connector according to claim 1, wherein the cover portions are in the form of flexible pouches.

10. The connector according to claim 1, wherein said connector member comprises plural connection members each having a connection end and a coupling end, and wherein said cover is adapted to encompass said plural connection members to provide for said aseptic seal.

11. The connector according to claim 1, wherein said connector comprises plural connector pairs or a connector manifold including plural paths for fluids and/or electricity.

12. The method for connecting and disconnecting one or more complementary pairs of connectors according to claim 1, the method comprising connecting the connector pair by:
   providing a cover on each connector which surrounds at least said coupling elements of the connector pair and forming a second seal by coupling a first seal member formed on a portion of the cover of a first of the connector pair to a second seal member formed on a portion of the cover of a second of the connector pair thereby isolating aseptically the complementary coupling elements of the connectors from their environment; and forming a first seal by coupling a coupling element on a coupling end of the first connector to a coupling element on a coupling end of the second connector, wherein at least one of the coupling ends is within the coupled seal members.

13. The method according to claim 12, wherein the coupling of the seal members to form the second seal comprises removing an overlying protective film from each of the seal members by pulling said films from between seal members after said seal members are initially coupled to create an essentially aseptic connection.

14. The method according to claim 12, further comprising mounting a cover portion comprising a seal member on or adjacent the coupling end of each connector before connecting the connectors.

15. The method according to claim 12, the method comprising disconnecting the connectors by disengaging the first seal by uncoupling of the coupling elements and separating the coupling ends so that none of them are within the seal members.

16. The method according to claim 15, the disconnecting further comprising sealing off an area of the cover of one or both connectors attached by means of aseptic sealing of each cover.

17. The method according to claim 16, wherein the aseptic sealing comprises heat sealing.

18. The method according to claim 12, further comprising:

removing the cover portion from the coupling end of one or more of the connector pair after disconnecting the connectors, and mounting a second cover portion on the coupling end of one or more of the connector pair.

19. An adapter comprising: a cover providing an aseptic enclosure for a coupling, the cover including at least two seals configured to be successively positioned on or adjacent an end of the coupling, providing multiple-use aseptic sealing around the coupling, and a further element configured to fit on, over, or adjacent the coupling, the further element being one of: a single-use seal element, a sealable mechanical coupling, or yet further at least two seals.

* * * * *